(12) United States Patent     (10) Patent No.:    US 12,622,684 B1

Alsoghier et al.     (45) Date of Patent:     May 12, 2026

(54) PUNCH BIOPSY TOOL WITH TRANSVERSE CUTTER AND ANGULAR ADJUSTMENT

(71) Applicant: KING SAUD UNIVERSITY, Riyadh (SA)

(72) Inventors: Abdullah Mohamed Alsoghier, Riyadh (SA); Nasser Raqe Alqhtani, Riyadh (SA); Ali Saleh Al Rafedah, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 89 days.

(21) Appl. No.: 19/055,791

(22) Filed: Feb. 18, 2025

(51) Int. Cl.

| | |
|---|---|
| *A61B 10/02* | (2006.01) |
| *A61B 10/06* | (2006.01) |
| *A61B 17/29* | (2006.01) |
| *A61B 17/3205* | (2006.01) |
| *A61B 18/00* | (2006.01) |
| *A61B 18/14* | (2006.01) |

(52) U.S. Cl.

CPC .......... *A61B 10/0266* (2013.01); *A61B 10/02* (2013.01); *A61B 2010/0208* (2013.01); *A61B 10/0233* (2013.01); *A61B 10/06* (2013.01); *A61B 2017/2905* (2013.01); *A61B 2017/2939* (2013.01); *A61B 17/32053* (2013.01); *A61B 2018/00601* (2013.01); *A61B 18/1442* (2013.01); *A61B 18/1445* (2013.01); *A61B 2560/0406* (2013.01); *A61B 2560/0425* (2013.01)

(58) Field of Classification Search

CPC . A61B 10/0266; A61B 10/02; A61B 10/0233; A61B 10/06; A61B 17/32053; A61B 18/1442; A61B 18/1445; A61B 2010/0208; A61B 2017/2905; A61B 2017/2939; A61B 2018/00601; A61B 2560/0406; A61B 2560/0425

See application file for complete search history.

(56) References Cited

U.S. PATENT DOCUMENTS

| | | | |
|---|---|---|---|
| 3,895,636 A | * | 7/1975 | Schmidt ........... A61B 17/32053 |
| | | | 606/205 |
| 4,200,111 A | * | 4/1980 | Harris .................... A61B 10/02 |
| | | | 600/564 |

(Continued)

*Primary Examiner* — Sean P Dougherty

(74) *Attorney, Agent, or Firm* — Nath, Goldberg & Meyer; Joshua B. Goldberg

(57) ABSTRACT

A punch biopsy tool includes an upper housing, lower housing, and a circular cutter attached to the lower housing configured to make a circular incision around a target tissue. A transverse cutter performs removal of the target tissue sample. An axially movable upper shaft member within the upper housing pivotally attaches to an intermediate linkage member. A lower linkage member is pivotally connected to an end of the intermediate linkage member. The transverse cutter may be formed by a pair of blades connected to the lower linkage member. Means for adjusting an angular orientation of the upper housing relative to the lower housing may be included such as an accordion shaped material or pivotable joint. Alternatively, the upper housing may be formed at a predetermined angle relative to the lower housing. The punch biopsy tool is suited for obtaining hard to reach tissue samples including, but limited to, oral lesions.

19 Claims, 3 Drawing Sheets

(56) References Cited

U.S. PATENT DOCUMENTS

| | | | | |
|---|---|---|---|---|
| 4,776,346 A * | 10/1988 | Beraha | A61B 10/0241 | 600/567 |
| 4,785,826 A * | 11/1988 | Ward | A61B 10/025 | 30/174 |
| 5,074,311 A * | 12/1991 | Hasson | A61B 10/06 | 600/568 |
| 5,119,818 A * | 6/1992 | Carroll | A61B 10/0233 | 250/336.1 |
| 5,342,390 A * | 8/1994 | Slater | H01L 21/67126 | 606/205 |
| 5,660,186 A * | 8/1997 | Bachir | A61B 10/0233 | 600/562 |
| 5,681,277 A * | 10/1997 | Edwards | A61B 18/00 | 604/22 |
| 5,860,995 A * | 1/1999 | Berkelaar | A61B 17/29 | 606/174 |
| 5,976,164 A * | 11/1999 | Bencini | A61B 10/0275 | 606/159 |
| 6,419,641 B1 * | 7/2002 | Mark | A61B 10/0275 | 600/564 |
| 7,588,545 B2 * | 9/2009 | Cohen | A61B 17/3462 | 600/564 |
| 9,872,642 B2 * | 1/2018 | Deck | A61B 5/685 | |
| 10,426,661 B2 * | 10/2019 | Kintz | A61F 9/008 | |
| 10,792,466 B2 * | 10/2020 | Landey | A61M 25/0136 | |
| 11,864,849 B2 * | 1/2024 | Chin | A61B 50/13 | |
| 12,023,013 B2 * | 7/2024 | Sharma | A61B 10/06 | |
| 2003/0040681 A1 * | 2/2003 | Ng | A61B 10/02 | 600/562 |
| 2003/0114773 A1 * | 6/2003 | Janssens | A61B 10/0233 | 600/564 |
| 2003/0225344 A1 * | 12/2003 | Miller | A61B 17/3496 | 600/568 |
| 2004/0002665 A1 * | 1/2004 | Parihar | A61C 9/00 | 600/587 |
| 2004/0087872 A1 * | 5/2004 | Anderson | A61B 10/0266 | 600/564 |
| 2005/0054947 A1 * | 3/2005 | Goldenberg | A61B 10/0266 | 600/567 |
| 2006/0047219 A1 * | 3/2006 | Baruti | A61B 10/0233 | 600/564 |
| 2006/0224082 A1 * | 10/2006 | Vetter | A61B 10/0233 | 600/431 |
| 2006/0224084 A1 * | 10/2006 | Vetter | A61B 10/0283 | 600/564 |
| 2007/0233047 A1 * | 10/2007 | Kerr | A61M 25/0097 | 604/539 |
| 2008/0058673 A1 * | 3/2008 | Jansen | A61B 17/221 | 600/567 |
| 2008/0234699 A1 * | 9/2008 | Oostman Jr. | A45D 26/00 | 606/133 |
| 2009/0018467 A1 * | 1/2009 | Chiu | A61B 10/0266 | 600/562 |
| 2009/0188150 A1 * | 7/2009 | Tomich | A01K 83/00 | 43/4.5 |
| 2009/0220601 A1 * | 9/2009 | Cutler | A61L 27/3839 | 424/484 |
| 2009/0236401 A1 * | 9/2009 | Cole | A61B 17/115 | 227/176.1 |
| 2010/0094166 A1 * | 4/2010 | Kraemer | A61B 10/0266 | 600/565 |
| 2010/0185116 A1 * | 7/2010 | Al-Mohizea | A61B 10/0233 | 600/564 |
| 2011/0105838 A1 * | 5/2011 | Fogel | A61B 10/0266 | 600/156 |
| 2011/0105947 A1 * | 5/2011 | Fritscher-Ravens | A61B 10/04 | 600/567 |
| 2012/0065543 A1 * | 3/2012 | Ireland | A61B 10/0275 | 600/567 |
| 2012/0157841 A1 * | 6/2012 | Glaenzer | A61B 10/0241 | 600/439 |
| 2012/0209303 A1 * | 8/2012 | Frankhouser | A61M 5/3287 | 606/169 |
| 2013/0090598 A1 * | 4/2013 | Vargas | A61B 17/3423 | 604/95.04 |
| 2013/0225943 A1 * | 8/2013 | Holsing | A61B 6/12 | 600/409 |
| 2015/0057572 A1 * | 2/2015 | Mendez-Coll | A61B 17/08 | 600/567 |
| 2015/0073300 A1 * | 3/2015 | Cao | A61B 10/0266 | 600/567 |
| 2015/0313692 A1 * | 11/2015 | Vizanski | A61C 8/0062 | 433/173 |
| 2017/0303889 A1 * | 10/2017 | Grim | A61B 8/0841 | |
| 2019/0254644 A1 * | 8/2019 | Mishra | A61B 17/295 | |
| 2019/0328370 A1 * | 10/2019 | Muse | A61B 10/0266 | |
| 2020/0100777 A1 * | 4/2020 | Mohanty | A61B 10/0266 | |
| 2022/0218320 A1 * | 7/2022 | Herrin | A61B 10/0283 | |
| 2023/0210505 A1 * | 7/2023 | Lonky | A61B 10/0291 | 600/569 |

* cited by examiner

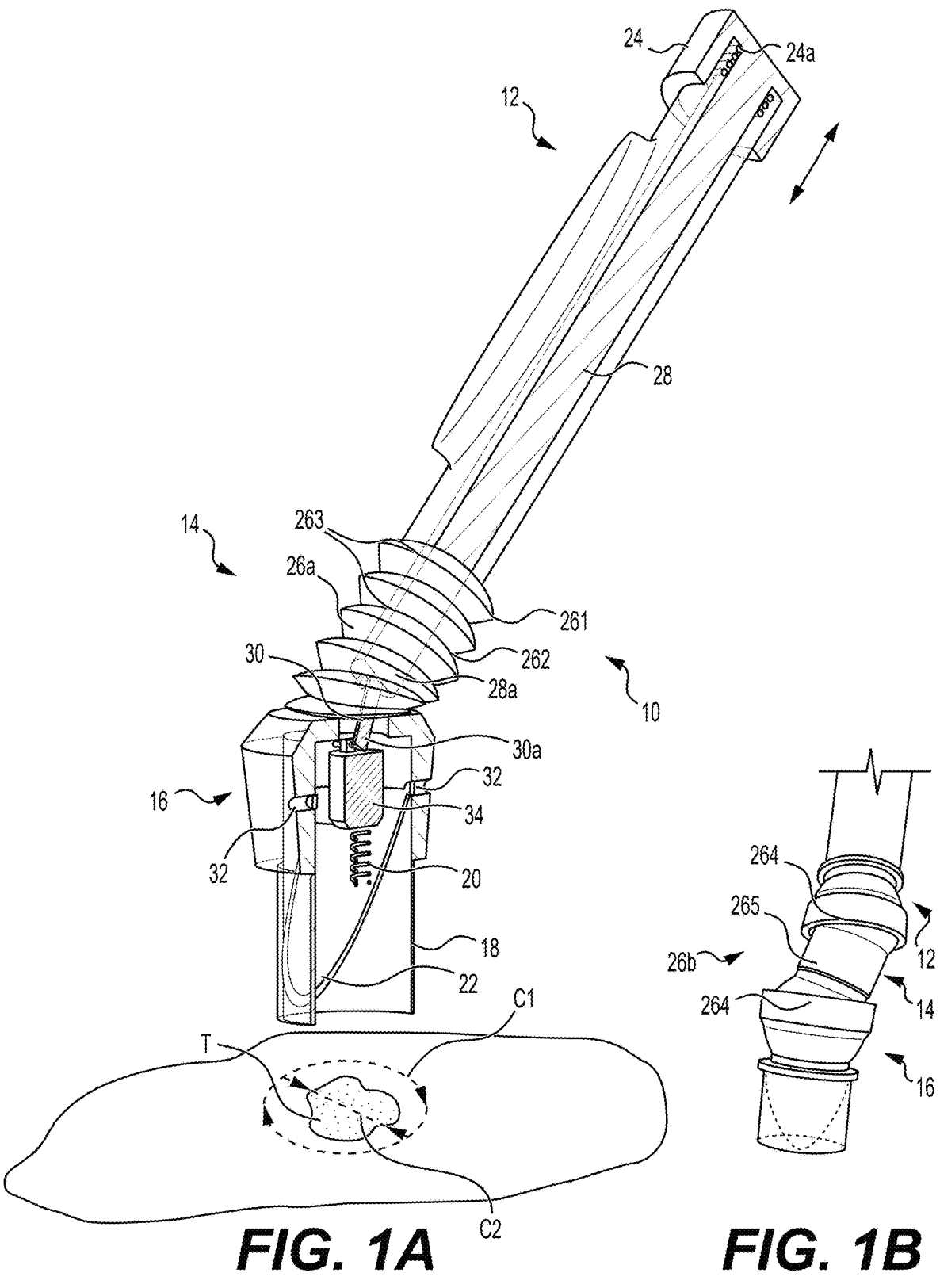
*FIG. 1A*          *FIG. 1B*

PUNCH BIOPSY TOOL WITH TRANSVERSE CUTTER AND ANGULAR ADJUSTMENT

BACKGROUND

Field

The disclosure of the present patent application relates to a biopsy device, and particularly to a punch biopsy tool having a circular cutter and transverse cutter as well as embodiments for angular adjustment thereof.

Description of Related Art

Oral cancer is often preceded by precursor lesions (e.g. oral leukoplakia and erythroplakia) and oral conditions (e.g. oral lichen planus). Such disorders may be diagnosed clinically but would also need a histopathological examination conducted through reviewing the tissue obtained from the oral cavity lining under a microscope to: 1) confirm or exclude the diagnosis; and, 2) to exclude the presence of dysplastic features of the oral epithelium. The presence of dysplastic features reflects architectural and cellular changes of the epithelial layers and can be classified as mild, moderate and severe dysplasia with an average of 12% increased risk of cancer.

Several non-invasive methods may be used to diagnose oral cancer and dysplastic changes, including using toluidine blue dye, oral brush biopsy, and saliva-based and light-based oral cancer detection technologies. However, surgical biopsy remains the gold standard for diagnosing various oral benign and malignant lesions.

The biopsy procedure can include surgical removal of the whole lesion (excisional) or certain areas (incisional) that show altered clinical morphology compared to the non-affected areas. The procedure may be done by use of a surgical blade or punch biopsy instrument, which is presently limited by the lack of a horizontal cutting edge specifically for oral mucosa tissue. A two-step procedure is typically required for using surgical blades and punch biopsy instruments involving first cutting with a circular punch blade and second capturing the tissue. To capture the tissue, the sample is lifted with a forceps and cut free from the underlying tissue using surgical scissors or a scalpel. Such instruments as described lack the angulation desired for the oral cavity, with most such biopsy instruments designed for use in other areas of the body.

An accurate histopathology assessment of biopsied lesions requires proper tissue sampling by choosing two adequate samples having the right size and depth, especially for varied clinical appearance. Acquiring samples of insufficient depth may not include the underlying stroma and, therefore, result in inappropriate histopathological assessment and clinical management, often requiring another procedure.

The advantages of using an oral punch biopsy include a precise tissue collection and reduced chance of sampling errors through the inclusion of a foreign body, which can be inadequately interpreted as cellular atypia. Nevertheless, limitations for using a punch biopsy tool include a crushing/tearing force caused by sharp instruments used to release the punched tissue sample, such as tissue forceps and surgical blades, as well as lack of angulation among prior punch biopsy instruments.

Thus, a punch biopsy tool with transverse cutting and angular adjustment solving the aforementioned problems is desired.

SUMMARY

In a non-limiting embodiment, a punch biopsy tool is provided including an upper housing, an intermediate housing, and a lower housing. A circular cutter is attached to the lower housing and configured to make a circular cut in tissue to be biopsied. A spiral shaped tissue grasper may be mounted within the circular cutter and lower housing for attaching to a target tissue area to be biopsied. Further provided is a transverse cutter for removal of the target tissue sample. The transverse cutter is attached to the lower housing and configured to make a transverse cut spanning a diameter of the circular cutter. A mechanical means such as for example, a button, are provided for actuating the transverse cutter. Means for adjusting an angular orientation of the upper housing relative to the lower housing are provided such as, for example, a flexible accordion shaped material, a flexible joint, or a pivoting joint forming the intermediate housing.

In a further non-limiting embodiment, the transverse cutter may include a pair of blades pivotally mounted to the lower housing. An axially movable upper shaft member may be provided within the upper housing as well as an intermediate linkage member pivotally connected to an end of the upper shaft member. A lower linkage member may be provided pivotally connected to an end of the intermediate linkage member. The pair of blades forming the transverse cutter may be connected to the lower linkage member and pivotally connected to the lower housing. The punch biopsy tool may include ergonomic gripping surfaces formed in the upper housing, and the circular cutter may include graduations on an outer surface thereof.

In another embodiment, a punch biopsy tool is provided including an upper housing and a lower housing. An upper shaft member is provided which is axially movable within the upper housing. Mechanical means such as a button are provided to axially move the upper shaft member within the upper housing. An intermediate linkage member is provided, which is pivotally connected to an end of the upper shaft member. A lower linkage member is pivotally connected to an end of the intermediate linkage member. A circular cutter is attached to the lower housing, and a transverse cutter is joined to the lower linkage member and pivotally connected to the lower housing.

An intermediate housing may be included as well as means for angular adjustment of the upper housing relative to the lower housing. The means for angular adjustment of the upper housing relative to the lower housing may include, for example, a flexible accordion-shaped material, pivotable joint, or other flexible joint forming the intermediate housing. Alternatively, the upper housing may be set at a fixed predetermined angle relative to the lower housing.

These and other features of the present subject matter will become readily apparent upon further review of the following specification.

BRIEF DESCRIPTION OF DRAWINGS

FIG. 1A is an environmental perspective cutaway view of a punch biopsy tool with transverse cutter and angular adjustment through a flexible accordion shaped housing.

FIG. 1B is a perspective view of a punch biopsy tool with transverse cutter and angular adjustment through a pivotable joint.

Similar reference characters denote corresponding features consistently throughout the attached drawings.

DETAILED DESCRIPTION

Figures 2A, 2B, 2C, 2D, 2E:
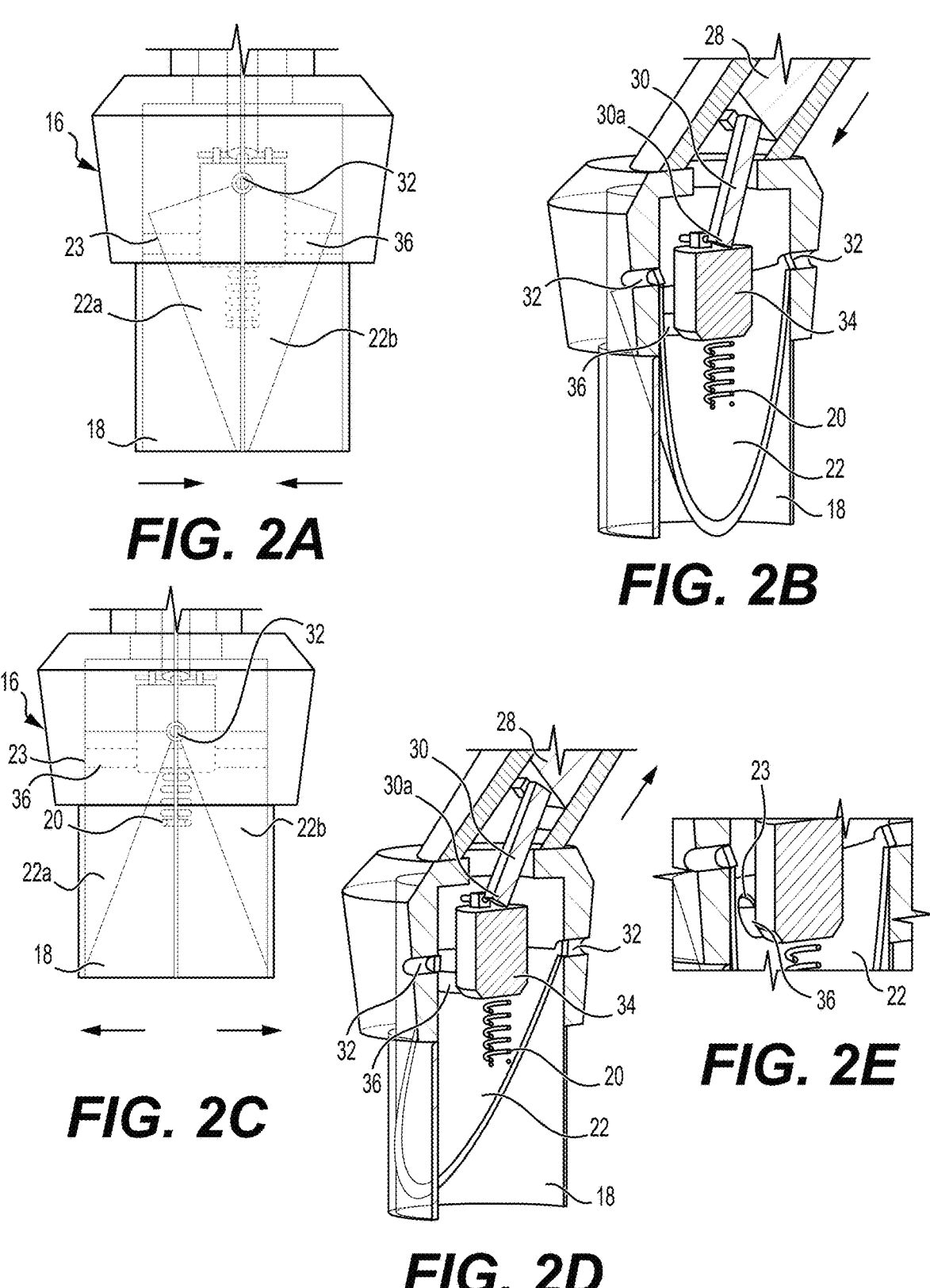
FIG. 2A is a front view of transverse cutter blades in a closed position.
FIG. 2B is a perspective cutaway view of a transverse cutter blade in a closed position.
FIG. 2C is a front view of transverse cutter blades in an open position.
FIG. 2D is a perspective cutaway view of a transverse cutter blade in an open position.
FIG. 2E is a perspective cutaway view of a radial arm joined to a transverse cutter blade through an opening formed in the blade.

With reference to FIG. 1, a punch biopsy tool 10 is provided including an upper housing 12, an intermediate housing 14, and a lower housing 16. A circular cutter 18 is attached to the lower housing 16 and configured to make a circular cut C1 around tissue T to be biopsied. A spiral shaped tissue grasper 20 formed with a pointed end may be mounted within the circular cutter 18 and lower housing 16 for attaching to a target tissue T by the rotating motion used for the circular cut C1. Further provided is a transverse cutter 22 for removal of the target tissue T following the circular cut C1. The transverse cutter 22 is attached to the lower housing 16 and configured to make a transverse cut C2 spanning a diameter of the circular cutter 18. A mechanical means such as, for example, a button 24 loaded by a spring 24a, are provided for actuating the transverse cutter 22. Other examples of mechanical means for actuating the transverse cutter may include a lever or sliding lever, a trigger, and an axially translating handle or finger loop, to name a few.

Means for adjusting an angular orientation of the upper housing 12 relative to the lower housing 16 are provided such as, by non-limiting example, a flexible accordion shape material 26a forming the intermediate housing 14. As used herein, "accordion shape", refers to a shape including peaks 261 defining an outermost diameter, valleys 262 defining an inner diameter, and annular ribs 263 formed by both peaks 261 and valleys 262. Flexible, accordion shape material 26a may be formed by one or more flexible materials including but not limited to thin stainless steel, aluminum, polyethylene or other plastic material, and/or silicon or other elastomeric material.

Alternatively, the means for adjusting an angular orientation of the upper housing 12 relative to the lower housing 16 may be provided in the form of a pivotable joint 26b, shown in FIG. 1B, including spherical joint connectors 264 and cylindrical portion 265. Pivotable joint 26b may be similar to that described in U.S. Pat. No. 4,776,617A, which is herein incorporated by reference. FIGS. 1A-B provide non-limiting examples of means for adjusting the angular orientation of upper housing 12 relative to lower housing 16, and any other means for adjusting the angular orientation may be used such as such as a braided stainless-steel connector, or other flexible or pivotable joint connection.

With reference to FIG. 1A and FIGS. 2A-E, in a non-limiting embodiment, the transverse cutter 22 may include a pair of blades 22a, 22b mounted to the lower housing 16 at pivot points 32. An axially movable upper shaft member 28 may be provided within the upper housing 12 and an intermediate linkage member 30 is pivotally connected to an end 28a (see FIG. 1A) of the upper shaft member 28. A lower linkage member 34 may be provided pivotally connected to an end 30a of the intermediate linkage member 30. The pair of blades 22a, 22b forming the transverse cutter 22 may be connected to the lower linkage member by radial arms 36 at openings 23 formed within blades 22a, 22b.

When upper shaft 28 is pushed downward by button 24, blades 22a, 22b are pushed inward (as shown in FIGS. 2A-B) by the downward motion transferred from upper shaft 28 to intermediate linkage member 30 to lower linkage member 34 and blades 22a, 22b through radial arms 36. Upon release of button 24 (shown in FIG. 1A), upper shaft member 28 is pushed upward by spring 24a, with the resulting motion moving blades 22a, 22b apart (as shown in FIGS. 2C-D) through upward motion of the shaft 28, linkage members 30, 34 and radial arms 36. Cutout holes 23 provide a slight clearance (shown in FIG. 2E) within which radial arms 36 are fitted, whereby the up and down motion of arms 36 within cutout holes 23 provides a camming force on blades 22a, 22b, causing blades 22a, 22b to pivot about pivot points 32.

Figures 3A, 3B, 3C:
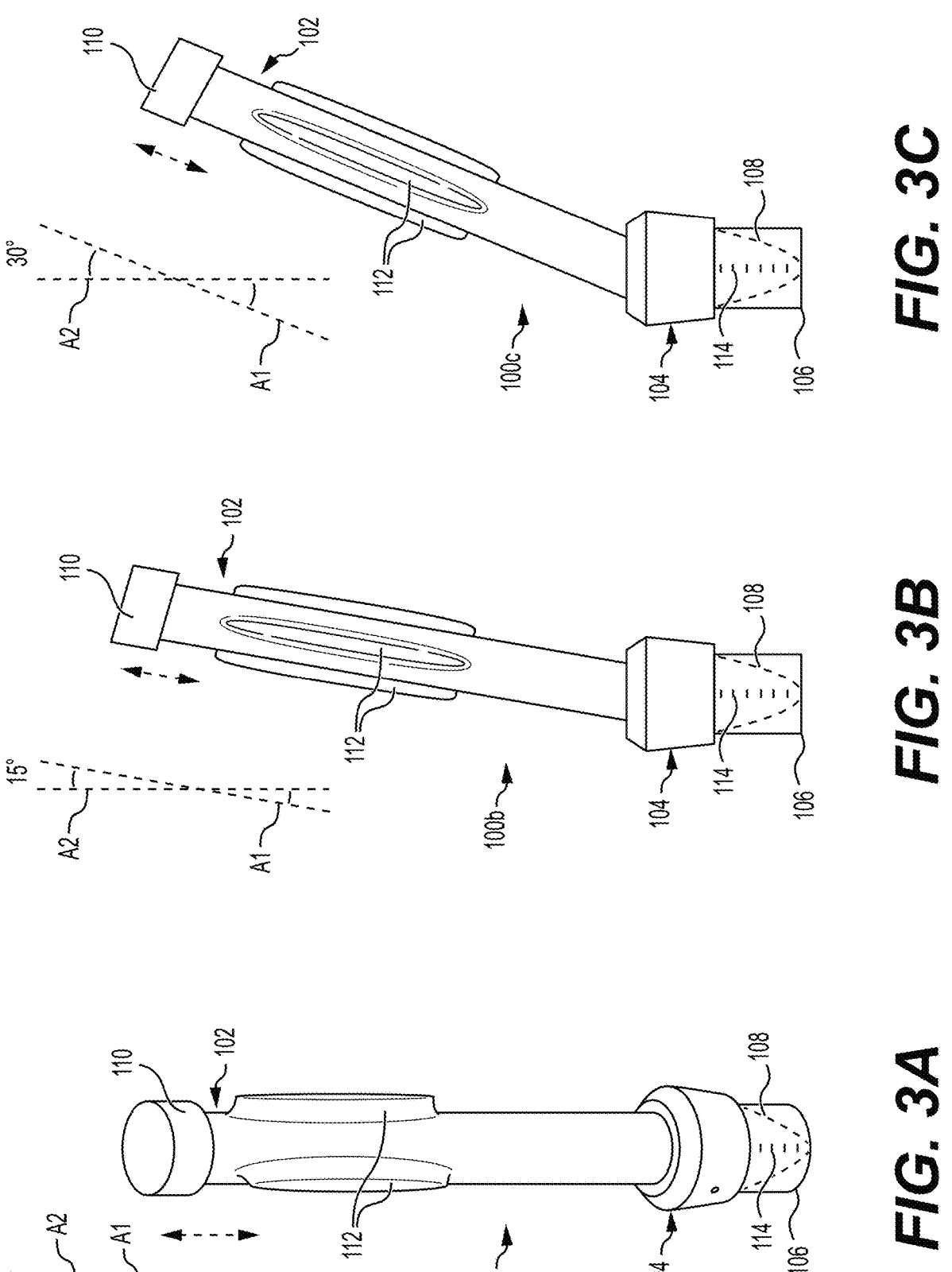
FIG. 3A is a font perspective view of a punch biopsy tool with a 0° angular orientation.
FIG. 3B is a side view of a punch biopsy tool with a 15° angular orientation.
FIG. 3C is a side view of a punch biopsy tool with a 30° angular orientation.

Referring now to FIGS. 3A-C, in another non-limiting embodiment, punch biopsy tools 100a-c are provided including an upper housing 102, a lower housing 104, and a circular cutter 106 attached to the lower housing 104. A transverse cutter 108 and means 110 of actuating the transverse cutter may be included. Internal elements not shown may be included, as previously discussed in the embodiment of FIGS. 1A-2E. However, in the embodiment of FIGS. 3A-C, the upper housing 102 may be set at a fixed predetermined angle with reference to lower housing 104. Such an embodiment may be used in a surgical procedure for biopsy removal as a complement or replacement to the embodiments of FIGS. 1A-B depending on the location and nature of the lesion to be removed. For instance, it may be desirable to use the embodiment of FIGS. 3A-C in situations where a greater force is sought in making the circular cut, without any loss of force to the circular cutter due to the means for angular adjustment as in the previous embodiment.

The punch biopsy tools 100a-c may be available in different set angles such, as 0°, 15°, and 30° represented in FIGS. 3A, 3B, and 3C respectively. The angles represent an orientation of the longitudinal axis A1 of the upper housing 102 to the longitudinal axis A2 of the lower housing 104 (and circular cutter 106). Of course, any set angle may be provided, as desired, besides the examples shown. The punch biopsy tools disclosed herein may include ergonomic gripping surfaces 112 formed in the upper housing 102. The circular cutter 106 of the punch biopsy tool may further include graduations 114 on an outer surface thereof for gauging a depth of incision into a target tissue area. Although not shown, the punch biopsy tool may be manufactured in a variety of sizes providing different diameters for the circular cutter 106. The diameter of the circular cutter 106 as well as the graduations 114 provide precise control of the size of the tissue sample to be obtained by the clinician, thereby allowing for capture of the underlying stroma and more accurate histopathological assessment of the obtained samples.

It is to be understood that the punch biopsy tool with transverse cutter is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A punch biopsy tool comprising:
an upper housing;
an intermediate housing;
a lower housing, wherein the upper housing, the intermediate housing and the lower housing together form an outer housing;
a circular cutter attached to the lower housing, wherein the circular cutter is configured to make a circular cut;
a transverse cutter pivotally attached within the lower housing and the circular cutter and configured to make a transverse cut spanning a diameter of the circular cutter;
mechanical means for actuating the transverse cutter; and
means for adjusting an angular orientation of the upper housing relative to the lower housing.

2. The punch biopsy tool according to claim 1, wherein the transverse cutter includes a pair of blades pivotally mounted within the lower housing.

3. The punch biopsy tool according to claim 1, wherein the means for adjusting angular orientation of the upper housing relative to the lower housing includes a flexible material having an accordion shape forming the intermediate housing, wherein the accordion shape includes peaks, valleys, and annular ribs formed by the peaks and valleys.

4. The punch biopsy tool according to claim 1, further comprising an upper shaft member axially movable within the upper housing and an intermediate linkage member having an upper end pivotally connected to a lower end of the upper shaft member, wherein the intermediate linkage member is positioned within the outer housing.

5. The punch biopsy tool according to claim 4, further comprising a lower linkage member having an upper end pivotally connected to a lower end of the intermediate linkage member, wherein the lower linkage member is positioned within the outer housing.

6. The punch biopsy tool according to claim 5, wherein the transverse cutter is formed by a pair of blades connected to the lower linkage member and pivotally connected to the lower housing.

7. The punch biopsy tool according to claim 6, further comprising a spiral-shaped tissue gripping attachment mounted within the lower housing.

8. The punch biopsy tool according to claim 7, wherein the means for adjusting an angular orientation of the upper housing relative to the lower housing is a flexible accordion shape material including peaks defining an outermost diameter, valleys defining an inner diameter, and annular ribs formed by the peaks and valleys.

9. The punch biopsy tool according to claim 3, wherein the flexible material having an accordion shape is formed from a material selected from the group consisting of a polymer, an elastomer, or an elastomeric material.

10. The punch biopsy tool according to claim 7, wherein the means for adjusting an angular orientation of the upper housing relative to the lower housing includes a pivotable joint including spherical joint connectors.

11. A punch biopsy tool comprising:
an upper housing;

an intermediate housing;
a lower housing, wherein the upper housing, the intermediate housing, and the lower housing form an outer housing;
an upper shaft member axially movable within the upper housing;
means for moving the upper shaft member axially within the upper housing;
an intermediate linkage member having an upper end pivotally connected to a lower end of the upper shaft member;
a lower linkage member having an upper end pivotally connected to a lower end of the intermediate linkage member, wherein the intermediate linkage member and the lower linkage member are positioned within the outer housing;
a circular cutter attached to the lower housing, wherein the circular cutter is configured to make a circular cut; and
a transverse cutter joined to the lower linkage member and pivotally connected to the lower housing within the circular cutter.

12. The punch biopsy tool according to claim 11, wherein a longitudinal axis of the upper housing is set at a predetermined slanted angle relative to a longitudinal axis of the lower housing.

13. The punch biopsy tool of claim 11, further comprising means for adjusting an angular orientation of the upper housing relative to the lower housing.

14. The punch biopsy tool of claim 13, wherein the means for adjusting an angular orientation of the upper housing relative to the lower housing includes a flexible accordion shaped material forming the intermediate housing, wherein the accordion shape includes peaks, valleys, and annular ribs formed by the peaks and valleys.

15. The punch biopsy tool according to claim 11, wherein the transverse cutter includes a pair of blades.

16. The punch biopsy tool according to claim 11, further comprising ergonomic gripping surfaces formed on the upper housing.

17. The punch biopsy tool according to claim 11, wherein the circular cutter includes graduations on an outer surface thereof.

18. A punch biopsy tool comprising:
an upper housing;
an upper shaft member axially movable within the upper housing;
a lower housing, wherein the upper housing and the lower housing form an outer housing;
an intermediate linkage member having an upper end pivotally connected to a lower end of the upper shaft member;
a lower linkage member having an upper end pivotally connected to a lower end of the intermediate linkage member, wherein the intermediate linkage member and the lower linkage member are positioned within the outer housing;
a circular cutter attached to the lower housing, wherein the circular cutter is configured to make a circular cut;
a transverse cutter pivotally attached within the lower housing and circular cutter;
mechanical means for actuating the transverse cutter; and
wherein the upper housing is positioned in a fixed predetermined slanted orientation relative to the lower housing.

19. The punch biopsy tool according to claim 18, wherein the transverse cutter is formed by a pair of blades.

* * * * *